United States Patent
Isaacson et al.

(10) Patent No.: US 9,144,472 B2
(45) Date of Patent: Sep. 29, 2015

(54) SYSTEM AND METHOD FOR EVALUATING ORTHODONTIC TREATMENT

(71) Applicants: Robert J. Isaacson, Edina, MN (US); Bruce W. Hultgren, Victoria, MN (US); Michael C. Marshall, Prior Lake, MN (US)

(72) Inventors: Robert J. Isaacson, Edina, MN (US); Bruce W. Hultgren, Victoria, MN (US); Michael C. Marshall, Prior Lake, MN (US)

(73) Assignee: Bruce W. Hultgren, Victoria, MN (US)

(*) Notice: Subject to any disclaimer, the term of this patent is extended or adjusted under 35 U.S.C. 154(b) by 76 days.

(21) Appl. No.: 13/623,754

(22) Filed: Sep. 20, 2012

(65) Prior Publication Data
US 2013/0273491 A1    Oct. 17, 2013

Related U.S. Application Data (63) Continuation of application No. 13/383,408, filed as application No. PCT/US2007/010839 on May 4, 2007, now abandoned.

(60) Provisional application No. 60/798,464, filed on May 4, 2006.

(51) Int. Cl.
*G06K 9/00* (2006.01)
*A61C 7/00* (2006.01)

(52) U.S. Cl.
CPC .. *A61C 7/002* (2013.01); *A61C 7/00* (2013.01)

(58) Field of Classification Search
None
See application file for complete search history.

(56) References Cited

U.S. PATENT DOCUMENTS

| | | |
|---|---|---|
| 5,882,192 A | 3/1999 | Bergersen |
| 6,217,334 B1 | 4/2001 | Hultgren |
| 6,250,918 B1 | 6/2001 | Sachdeva et al. |
| 6,413,083 B1 | 7/2002 | Hamilton |
| 6,579,059 B2 | 6/2003 | Chen |

(Continued)

FOREIGN PATENT DOCUMENTS

| | | |
|---|---|---|
| EP | 2 020 951 | 2/2009 |
| WO | WO 94/10935 | 5/1994 |

(Continued)

OTHER PUBLICATIONS

U.S. Appl. No. 11/800,430, filed May 2007, Hultgren et al.
(Continued)

*Primary Examiner* — Nirav G Patel
(74) *Attorney, Agent, or Firm* — Merchant & Gould P.C.

(57) ABSTRACT

A system and method for evaluating dental treatment utilizes virtual models created from scanned plaster casts. Patient's teeth are directly scanned with a three dimensional scanner or plaster casts of the patient teeth following treatment are scanned for evaluation. A planned configuration based on a plaster cast prior to treatment is created and the desired position and the two models are compared so that the actual position of the teeth may be compared to the desired position after treatment. Superimposition of the virtual models provides accurate and precise measurement of variances between the two virtual models. Difficulties due to superimposing the models, which are of the entire arch and evaluations based on individual teeth are overcome by applying an iterative closest point algorithm to correct the position and provide a truer measurement for evaluation. Differences between a preferred position of a patient's teeth and actual position of a patient's teeth may be assigned a score and the score may be compared to other patients to rank the patient needs.

16 Claims, 10 Drawing Sheets

(56) References Cited

U.S. PATENT DOCUMENTS

| | | |
|---|---|---|
| 6,602,070 B2 | 8/2003 | Miller et al. |
| 6,632,089 B2 | 10/2003 | Rubbert et al. |
| 7,029,275 B2 | 4/2006 | Rubbert et al. |
| 7,080,979 B2 | 7/2006 | Rubbert et al. |
| 7,210,929 B2 | 5/2007 | Raby et al |
| 7,744,369 B2 | 6/2010 | Imgrund et al. |
| 8,108,189 B2 | 1/2012 | Chelnokov et al. |
| 8,401,826 B2 | 3/2013 | Cheng et al. |
| 2002/0025503 A1 | 2/2002 | Chapoulaud et al. |
| 2002/0031742 A1 | 3/2002 | Hamilton |
| 2002/0064748 A1 | 5/2002 | Chishti et al. |
| 2004/0029068 A1 | 2/2004 | Sachdeva et al. |
| 2004/0038168 A1* | 2/2004 | Choi et al. ............ 433/24 |
| 2004/0259049 A1 | 12/2004 | Kopelman et al. |
| 2006/0263739 A1* | 11/2006 | Sporbert et al. ........ 433/24 |
| 2006/0263741 A1 | 11/2006 | Imgrund et al. |
| 2007/0154866 A1* | 7/2007 | Hall .................... 433/213 |
| 2008/0057462 A1 | 3/2008 | Kitching et al. |
| 2008/0286712 A1 | 11/2008 | Imgrund et al. |
| 2009/0061382 A1 | 3/2009 | Wen |
| 2009/0098502 A1 | 4/2009 | Andreiko |
| 2010/0145664 A1 | 6/2010 | Hultgren et al. |
| 2010/0169057 A1 | 7/2010 | Hultgren et al. |
| 2011/0189625 A1 | 8/2011 | Hultgren |
| 2011/0191075 A1 | 8/2011 | Hultgren |
| 2011/0244415 A1 | 10/2011 | Batesole |

FOREIGN PATENT DOCUMENTS

| | | |
|---|---|---|
| WO | WO 03/094102 A1 | 11/2003 |
| WO | WO 07/130573 A2 | 11/2007 |
| WO | WO 07/130574 A1 | 11/2007 |

OTHER PUBLICATIONS

U.S. Appl. No. 11/999,891, filed Dec. 2007, Isaacson et al.
U.S. Appl. No. 12/169,567, filed Jul. 2008, Isaacson et al.
U.S. Appl. No. 12/359,993, filed Jan. 2009, Isaacson et al.
U.S. Appl. No. 12/299,581, filed Nov. 2008, Hultgren.
U.S. Appl. No. 11/999,892, filed Dec. 2007, Isaacson et al.
U.S. Appl. No. 11/800,449, filed May 2007, Isaacson et al.
U.S. Appl. No. 13/383,408, filed Jan. 2012, Isaacson et al.
Vardimon, A. et al., "Cortical bone remodeling/tooth movement ratio during maxillary incisor retraction with tip versus torque movements," *Am. J. Orthod. Dentofacial Orthop.*, vol. 114, No. 5, pp. 520-529 (Nov. 1998).
George Papaioannou, NPL Publication, "Joints, Biomechanis of", 63 pages, (Feb. 2006).
Jan Edwards, "Rotation and Translation of the Jaw During Speech", 16 pages, (1990).
Kazuo Hayashi, "Simulation Study for a Finite Helical Axis Analysis of Tooth Movement" 6 pages, (2005).
International Search Report in PCT/US2007/010839 mailed Oct. 17, 2007.
International Search Report in PCT/US2007/010838 mailed Jul. 11, 2007.

* cited by examiner

SYSTEM AND METHOD FOR EVALUATING ORTHODONTIC TREATMENT

This application is being filed on 4 May 2007, as a PCT International Patent application in the name of Robert J. Isaacson, Bruce Willard Hultgren, Michael-Craig Marshall, and James E. Beauchamp, all citizens of the U.S., applicants for the designation of all countries, and claims priority to U.S. Provisional Patent Application No. 60/798,464, filed May 4, 2006.

BACKGROUND OF THE INVENTION

1. Field of the Invention

The present invention is directed to a system and method for evaluating orthodontic treatment in an objective manner by comparing virtual models of teeth following orthodontic treatment to a targeted alignment.

2. Description of the Prior Art

Evaluation of patient's needs and treatment is invaluable for determining a prognosis and diagnosis for the patient. Precise and accurate measurement of a patient's teeth is needed for diagnosis and for evaluation. Traditional methods require locating selected patient structures and using the structures as landmarks. The use of landmarks has built in imprecision as there is some imprecision in locating the landmark twice. The problem is compounded when the landmark must be located after growth and/or treatment. Therefore, it has been difficult for practitioners to quantify and rate severity or to quantify treatment success.

Evaluation and grading also is important for ensuring that orthodontic practitioners are performing satisfactorily. In order to ensure quality standards are maintained, the American Board of Orthodontics (ABO) certifies members who pass a stringent examination including a clinical examination. The clinical examination currently involves reviewing casts from patients to assess the success and quality of the treatment provided. An objective grading system has been developed to evaluate final dental casts and radiographs. Criteria and areas evaluated include alignment, marginal ridges, buccolingual inclination, occlusal relationships, occlusal contacts, overjet, interproximal contacts and root angulation.

The evaluation is conducted by a group of members of the American Board of Orthodontics utilizing a specially developed measuring gauge. Members of the ABO involved in grading the clinical examination take measurements on various locations on several sets of plaster casts presented by candidates seeking certification. Graders make determinations regarding deviation from a desired result and points are awarded according to the success of the treatment. A score is then assigned for the clinical examination.

For each candidate, ten or more cases may be evaluated. For each case, the upper arch and lower arch are measured, meaning that more than twenty sets of measurements are made and compared for each candidate. It can be appreciated that with many candidates seeking certification and a number of graders involved in the certification, the clinical examination grading process is a time consuming endeavor than can take hundreds of man hours for each examination.

In addition to being time consuming, the examination process has several flaws. The manual measurements that are made may not be consistent from grader to grader. Precisely locating landmarks for reference points used in comparison is challenging. In addition, there is subjectivity with regard to the results and further inaccuracies that may be incorporated from the measurement process. Due to these drawbacks, it is possible for some candidates who should pass the certification process to be failed while others may pass that should not.

It can be seen that a new and improved system and method for quantifying the severity of a patient's condition and for grading orthodontic treatment is required. In addition, a method and system is needed that provides a precise and objective evaluation with a numerical rating comparing the position of the teeth to an ideal position. Such a system should eliminate the need to use traditional landmarks to make measurements while increasing accuracy and consistency over prior art manual measuring systems. Moreover, such a system should provide for greater precision than is possible with the current systems. Such a system should eliminate the need for each grader to manually measure and evaluate the final occlusion and allow all graders to utilize an accurate virtual model. Such a system should save time and effort over current systems. In addition, such an evaluation system and method should provide an electronic model suitable for use beyond grading for examination purposes. The present invention addresses these problems, as well as others associated with evaluation of orthodontic treatment.

SUMMARY OF THE INVENTION

The present invention is directed to a system and method for evaluating the success of orthodontic treatment with electronic modeling. According to the present invention, digital models of a patient's teeth are created prior to treatment. A treatment plan is then formulated and an electronic plan with an idealized model is created with a digital representation of a final ideal position of the teeth.

The three dimensional digital model of the patient's teeth following treatment is then superimposed with the idealized model. As there are inconsistencies with superimposing the entire arch, which is treated as a single element, certain individual teeth may appear to be unduly out of alignment. Therefore, a best fit matching process is performed utilizing data of the coordinates representing the teeth. The matching program uses a best fit algorithm, such as an iterative close point algorithm to move each of the teeth individually for matching. It has been found that the algorithm typically needs to be run five times and there is virtually no movement of the teeth after ten iterations. The moved teeth are then superimposed and variances are measured. The variances can then be represented in a three dimensional electronic image. It can be appreciated that the position and translation of a tooth and its coordinate system may be changed by the closest point matching algorithm. However, it has been found that the matching process compensates for possible errors due to matching a cast of the entire arch.

Following application of the matching program, the electronic images are superimposed with a mesh of measurement points on the surface of the tooth matched for evaluation. The virtual model can accurately and precisely measure the virtual distance between the measurement points in three dimensions and that distance is determined for each point. A numerical score may then be assigned corresponding to the variance. Variances for all the grading criteria are then determined and scores assigned. The numerical scores for all the criteria and all the teeth may then be added together to give a final score for evaluation. This data and the assigned scores are then utilized for evaluating the overall success of the treatment.

In addition to measuring the differences between an actual position and an ideal position of a tooth or other structure, it is also advantageous to evaluate the fit of the teeth. The contacts points of a patient's idealized teeth can be compared to actual contact points as the contact points can be precisely captured with scanning to create the virtual models.

A numerical score may also be given between the idealized model and the model taken before treatment. This score provides for an objective evaluation of the severity of the corrections needed and may be used to prioritize treatment, expenditures, likelihood of success and/or to compare the needs of one patient as compared to another.

These features of novelty and various other advantages that characterize the invention are pointed out with particularity in the claims annexed hereto and forming a part hereof. However, for a better understanding of the invention, its advantages, and the objects obtained by its use, reference should be made to the drawings that form a further part hereof, and to the accompanying descriptive matter, in which there is illustrated and described a preferred embodiment of the invention.

DETAILED DESCRIPTION OF THE PREFERRED EMBODIMENT

Figure 1:
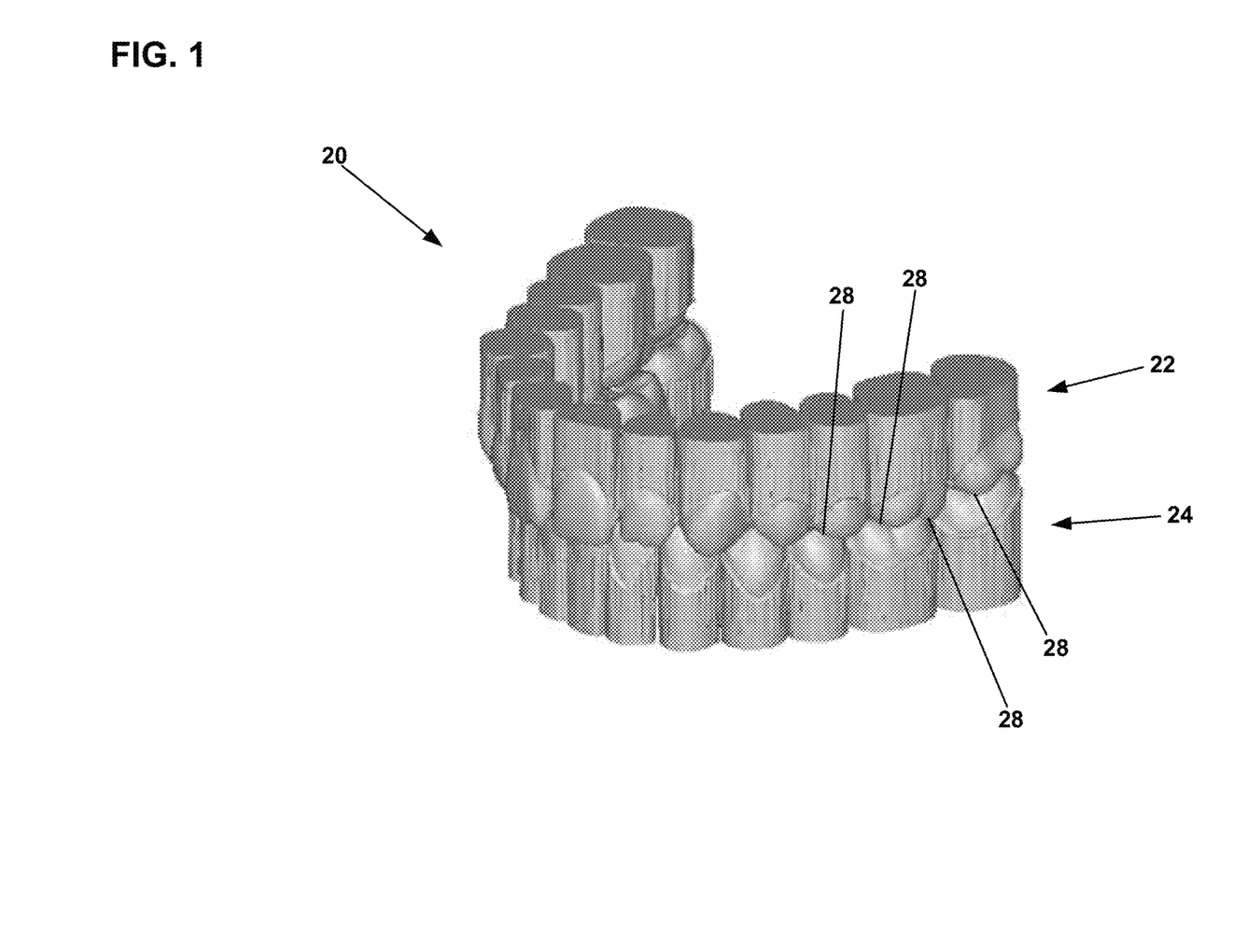
FIG. 1 is a perspective view of a virtual model of the upper and lower arches of a patient according to the principles of the present invention.

Referring now to the drawings and in particular to FIG. 1, there is shown a scanned digital representation 20 of a patient's complete upper and lower arches, 22 and 24. Such a digital representation of a patient's teeth is sold under the trademark E-Model®, owned by Geodigm Corporation of Chanhassen, Minn. The method and system for creating such a virtual image is shown and described in U.S. Pat. No. 6,579,059. The virtual model 20 may be created by first taking a conventional plaster cast of the patient's upper and lower arches. The cast is then electronically scanned and saved as a three dimensional virtual model. Such models provide an excellent tool for evaluation by the dental practitioner. Such digital models provide benefits by storing an accurate record of the patient's teeth and gums without requiring space or a suitable controlled environment for storing the plaster casts. Moreover, the digital models allow for precise measurement from the virtual surfaces for evaluation.

More recently, high resolution three dimensional scanners have been developed that provide three dimensional craniofacial imaging that may be used to create a digital representation of a patient's teeth with a high degree of precision without plaster casts and without using landmarks or markers. Such scanners include cone beam tomography scanners, intra-oral scanners, CT scanners and other technologies that provide high resolution precision three dimensional digital models. Examples of commercially available scanners include cone beam scanners sold under the trade names ILUMA™ from Kodak and i-CAT from Imaging Sciences International. Cone beam tomography scanners are well suited for such applications as they emit lower radiation than traditional dental x-rays and may eliminate the need for creating plaster casts.

Figure 4:
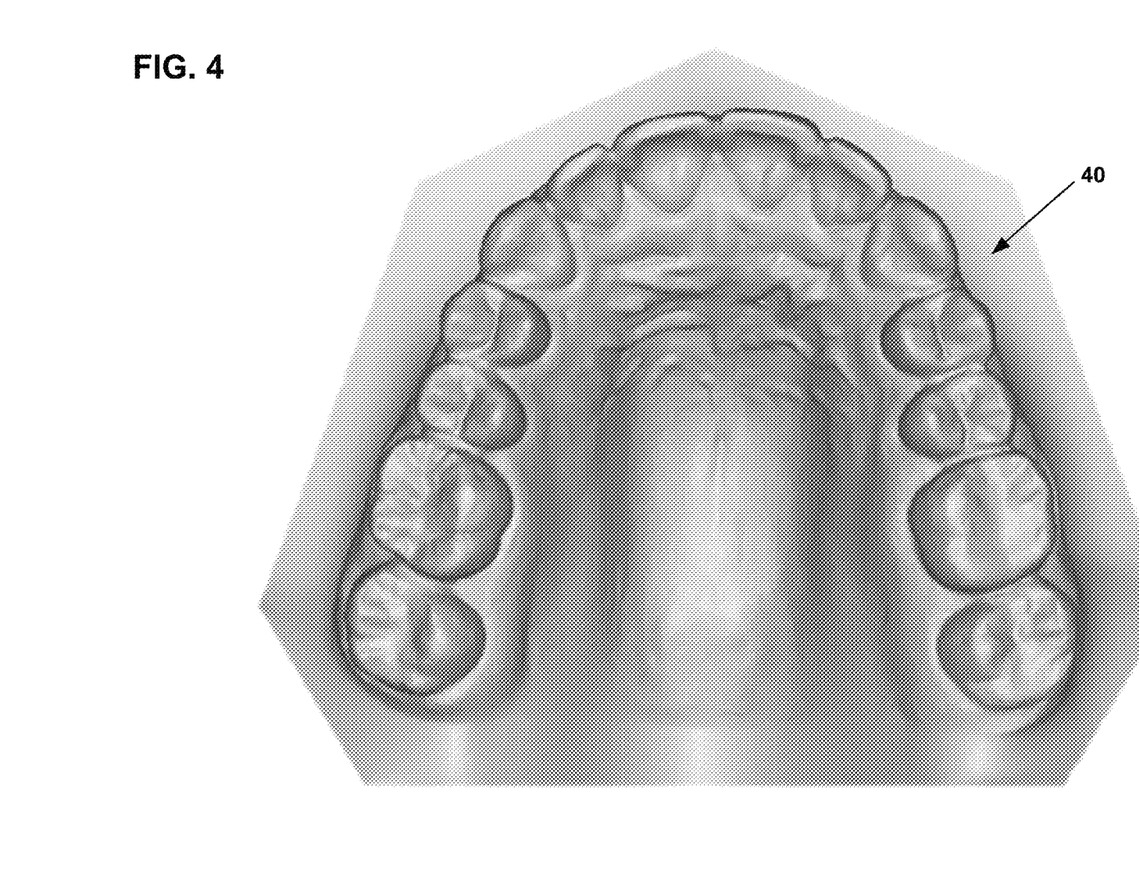
FIG. 4 is an electronic representation of a dental model with desired positioning following treatment for the virtual model shown in FIG. 2.
Figure 5:
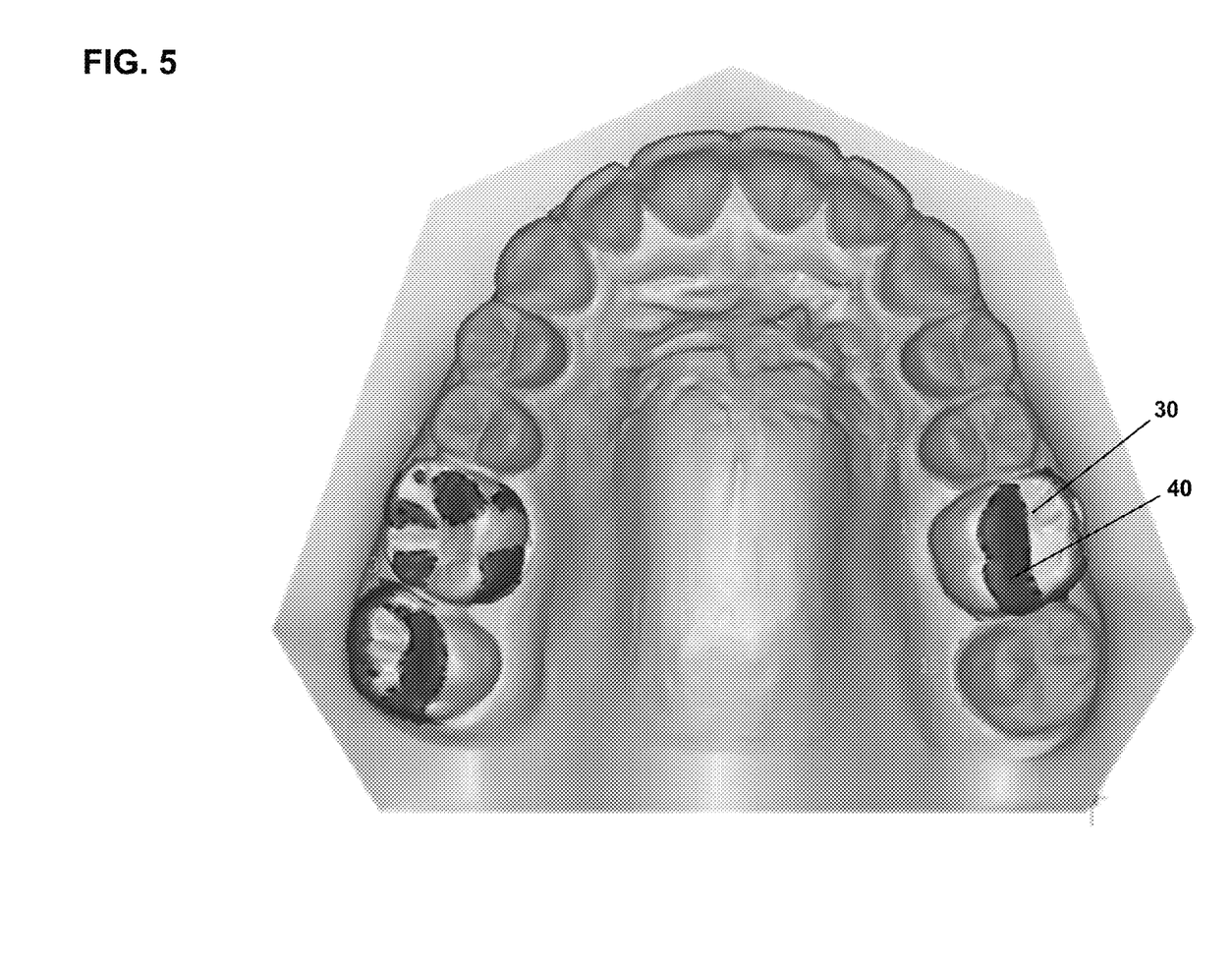
FIG. 5 is a perspective view of the electronic representation of the desired arch configuration shown in FIG. 4 being superimposed to the virtual model shown in FIG. 2.

It can be appreciated that plaster casts are currently taken before and after treatment and used for grading by the American Board of Orthodontics. The before and after plaster casts may be digitized and stored. Based on the original casting before treatment, a desired treatment outcome may be created from the digital model by moving each of the teeth to a desired position and alignment 30 such as shown in FIG. 4. Such a virtual electronic representation 30 of a desired final result is marketed under the trademark EPLAN® owned by Geodigm Corporation of Chanhassen, Minn. With the digitized, three dimensional models, it is possible to precisely locate individual teeth and determine how much movement of each tooth is needed.

Figure 2:
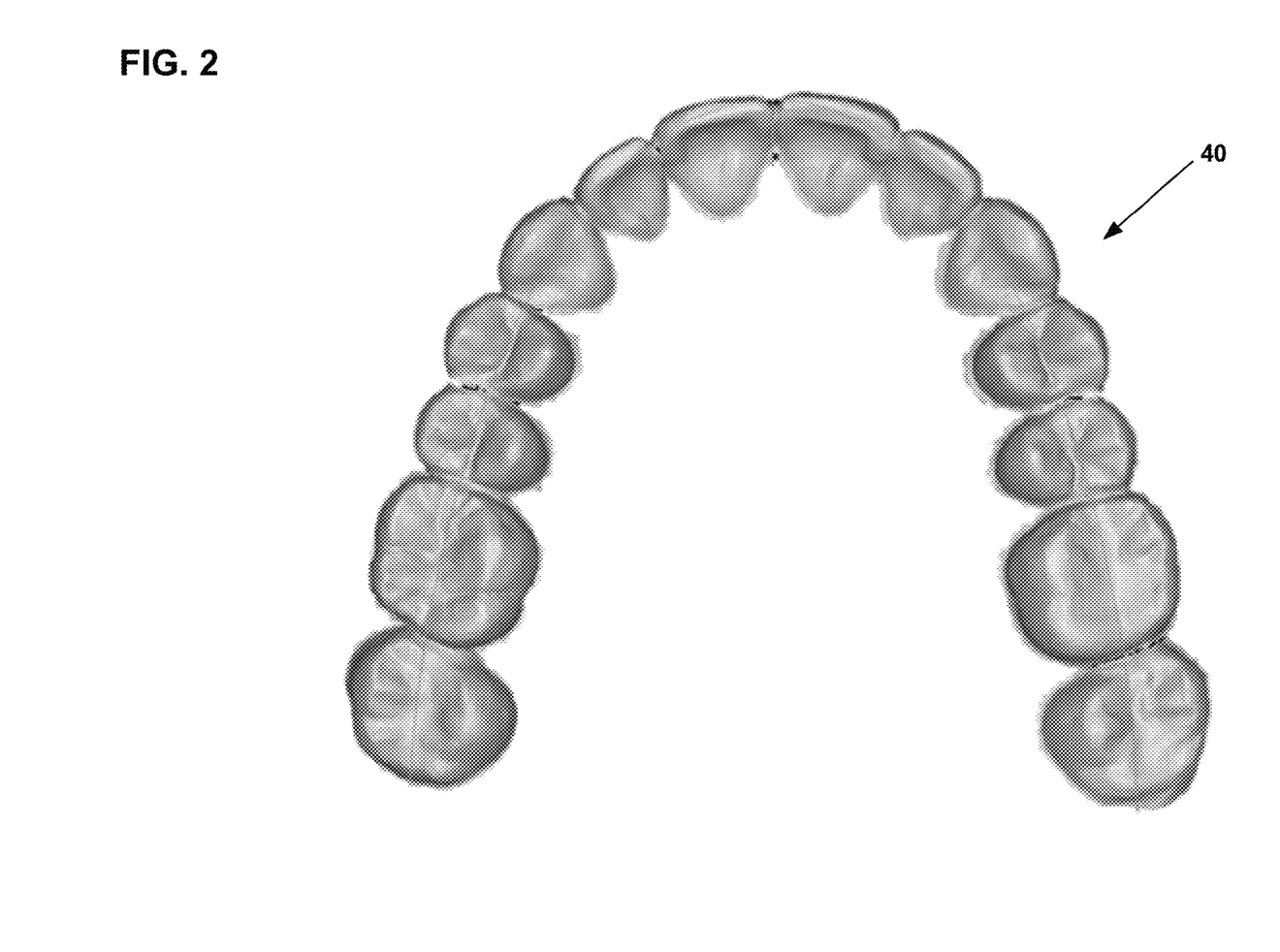
FIG. 2 is a plan view of an electronic virtual dental model following treatment according to the principles of the present invention.
Figure 3:
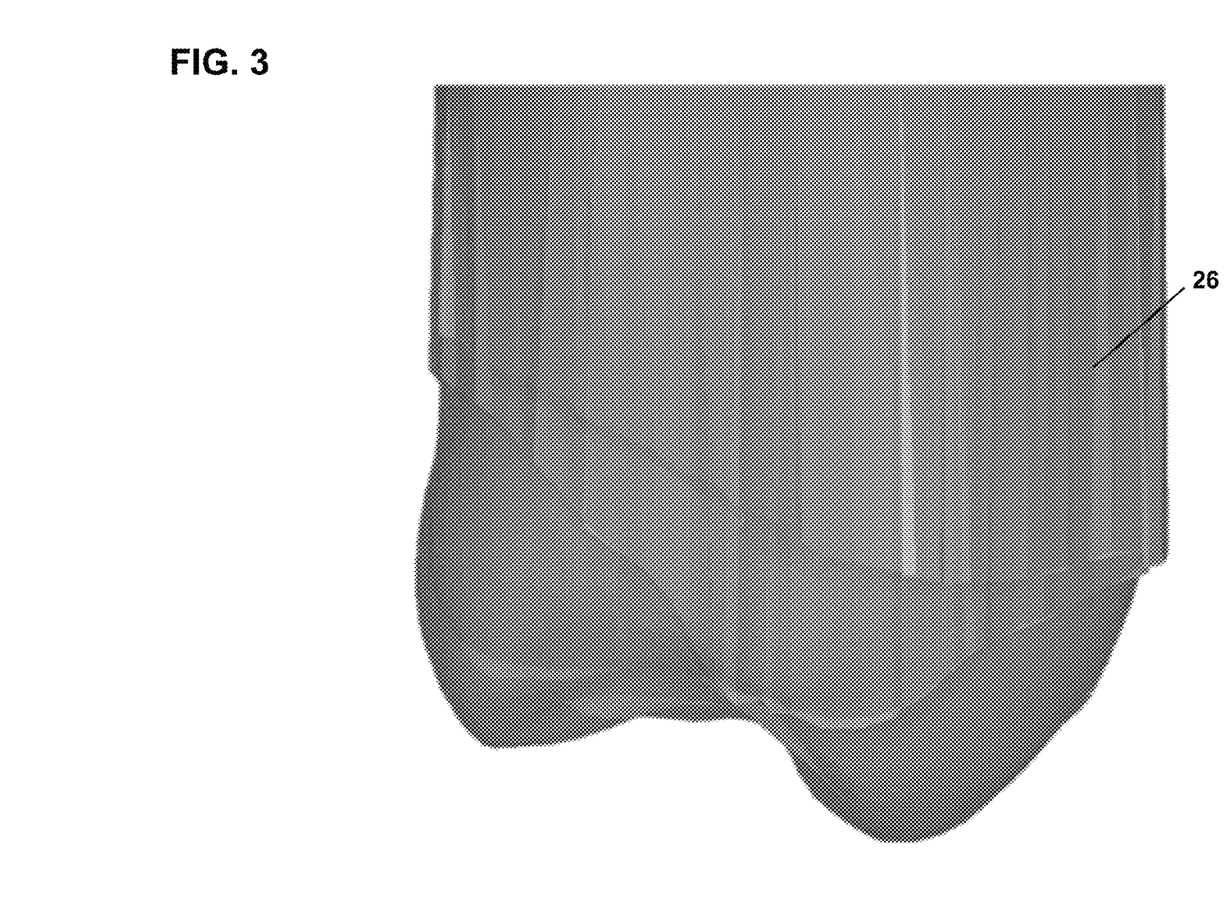
FIG. 3 is a side view of a single tooth of the virtual model shown in FIG. 2 with a three dimensional coordinate system applied.

It can also be appreciated that such a virtual model 30 representing desired results of treatment shown in FIG. 4 and a digital model 40 of the actual results of treatment represented by FIG. 2 may be compared to evaluate the treatment. The virtual electronic models 20, 30 and 40 also provides for applying a coordinate system to each tooth 26 as shown in FIG. 3, so that in addition to location, the orientation, rotation and other criteria may also be evaluated. Scores relating to the differences may be assigned for each variable. Each tooth will have six variable, one for movement in three dimensions and one for rotational movement about threes axes. For some applications, each tooth 26 will have a dedicated coordinate system whose orientation may change or a master coordinate system for all teeth may be used for some types of evaluation. A score may be generated for each tooth using the 6 possible degrees of freedom and a total score for the patient may be generated for all teeth based on the sum of 168 values, six possible scores for each of twenty eight teeth.

In addition, to movement of each tooth and other structures is the occlusion between the upper and lower teeth that affects the patient's bite. The virtual models provide a precise location of contact points 28, shown in FIG. 1. The idealized virtual model also includes virtual idealized contact points. The actual contact points can be compared to the idealized contact points and the differences determined and given a numerical value. This score can be used along with the other scores for more in depth evaluation. The contact points from the initial bite and the post treatment bite can be compared to the contact points of the idealized bite. Although a coordinate system is relative when there are multiple discreet elements, as the cranial face of a patient is substantially unchanged after about six years of age, a virtual model provides a reliable reference coordinate system to aid in positioning the set of upper teeth and lower teeth for an accurate and precise comparison and for improved evaluation of treatment as well as growth and development.

For treatment, each tooth has a mesh of selected points, preferably on the top of the tooth, that are selected. The tooth is also assigned an XYZ coordinate system based on its shape and the measurement points in the mesh. This is shown for example, in FIG. 3, with electronic representation of a tooth 26.

Figure 6:
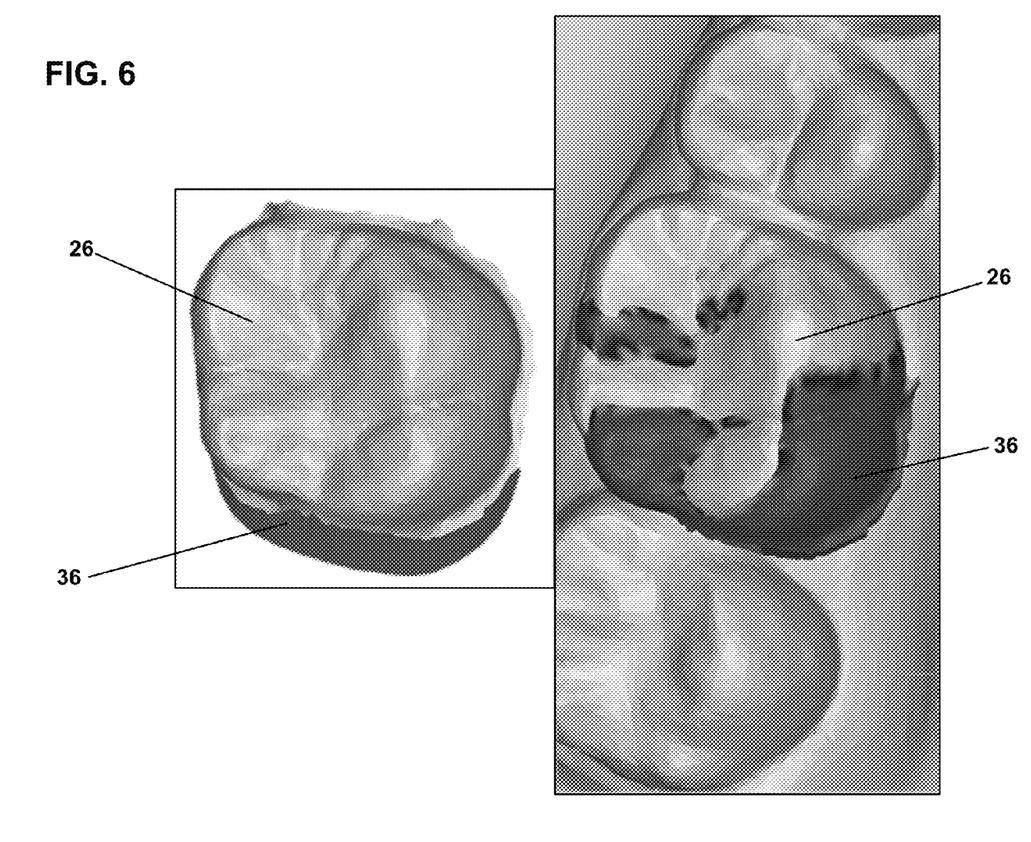
FIG. 6 is an electronic representation of a tooth superimposed on the arch showing differences in position.
Figure 7:
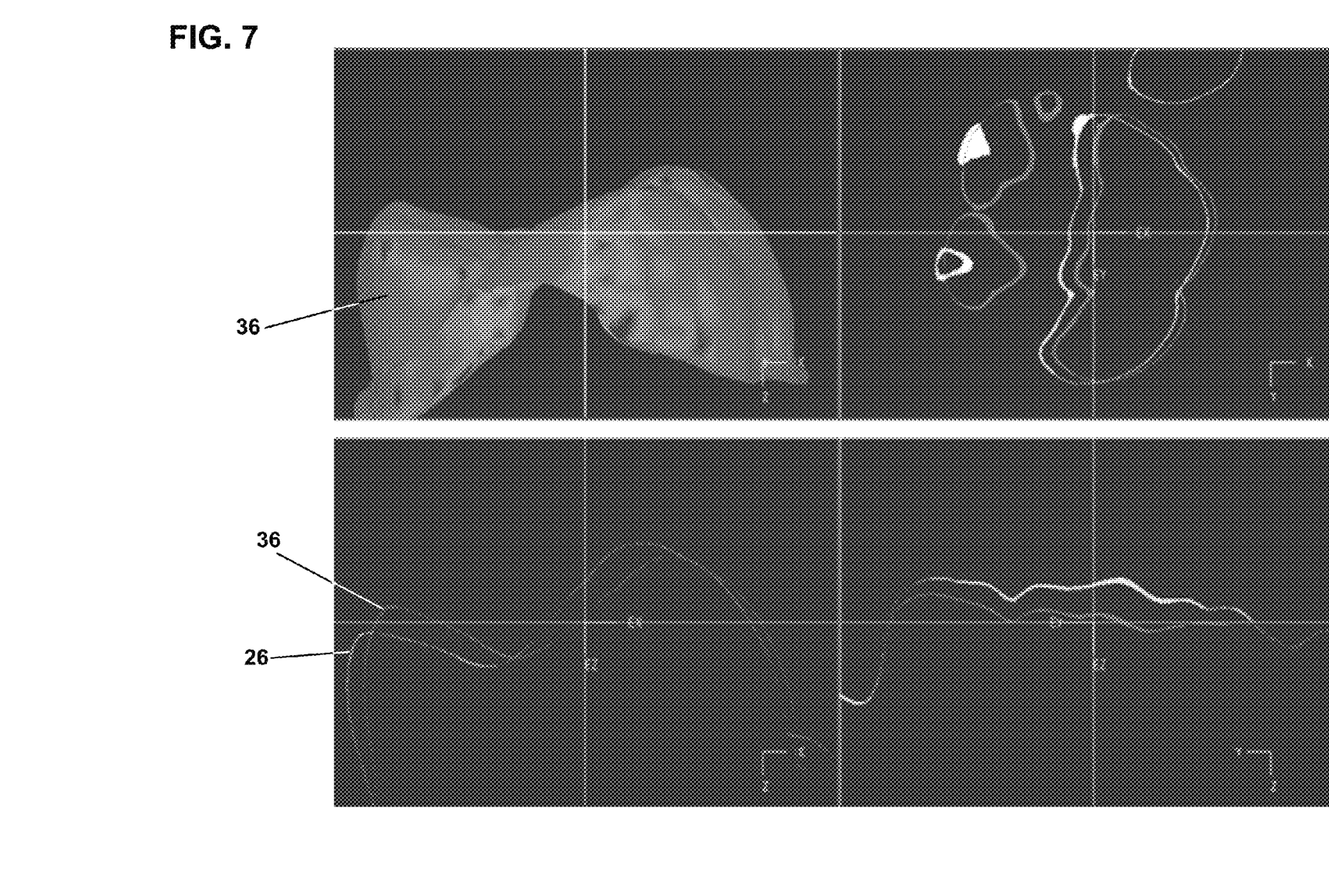
FIG. 7 is a cross-sectional view of a virtual model of a portion of a tooth with differences shown between the desired position and actual position following treatment.

The arch of the electronic plan 30 is then superimposed on the virtual model of the patient's post treatment arch 40. When the arches are superimposed, individual differences between the teeth can be measured with great precision in three dimensions using the electronic digital model. Such variances are shown in FIGS. 6 and 7. The differences can be assigned numerical values based on distance that may be utilized in evaluation and grading to achieve an objective score. The measurements also provide for extrapolation of data for the other grading criteria. Although such a process and method is helpful, there are some drawbacks as the superimposition of the digital images creates some inaccuracies for individual teeth. It can be appreciated that finding proper fit and alignment for measuring differences is a challenge as one or more of the teeth will have moved either in position and/or orientation. Moreover, the alignment of the upper and lower arches affects the final position. To provide improved matching, a matching process is conducted using an iterative of closest point algorithm. Such a best fit matching compensates for possible inaccuracies in matching the virtual model of the entire arch rather than individually matching the positions of each tooth.

An example of a suitable best fit program is an iterative closest point algorithm. The iterative closest point algorithm is an iterative alignment algorithm that works in three phases: 1) establish correspondence between pairs of features in the two structures that are to be aligned based on proximity, 2) estimate the rigid transformation that best maps the first member of the pair onto the second and then 3) apply that transformation to all features in the first structure. These three steps are then reapplied until convergence is concluded. Although simple, the algorithm works quite effectively when given a good initial estimate.

More precisely, such a point matching algorithm is represented by:

Let $\mathcal{S}$ be a set of $N_s$ points $\{\vec{s}_1, \ldots, \vec{s}_{N_s}\}$ and $\mathcal{M}$ be the model. Let $\|\vec{s} - \vec{m}\|$ be the Euclidean distance between point $\vec{s} \in \mathcal{S}$ and $\vec{m} \in \mathcal{M}$. Let $CP(\vec{s}, \mathcal{M})$ be the closest point in $\mathcal{M}$ to the scene point $\vec{s}$.

1. Let $T^{[0]}$ be an initial estimate of the rigid transformation.
2. Repeat for $k=1 \ldots k_{max}$ or until convergence:
   1. Compute the set of correspondences $$C = U_{i=1}^{N_s}\{(\vec{s}_i, CP(T^{[k-1]}(\vec{s}_i), \mathcal{M}))\}.$$

2. Compute the new Euclidean transformation $T^{[k]}$ that minimizes the mean square error between point pairs in C.

The basic algorithm has been previously extended in a number of ways: 1) correspondence between a point and a tangent plane to overcome the lack of an exact correspondence between the two sets, 2) robustifying the algorithm to the influence of outliers and features lacking correspondences, 3) using a weighted least-square error metric, and 4) matching between features using a metric trading off distance and feature similarity (based local shape invariances). All of these approaches assume a rigid Euclidean transformation between the corresponding features, whereas the method presented here uses projective correspondence.

This process is known as "wiggling" and is believed to provide a truer representation of the success of treatment. The application of the closest point algorithm to each tooth provides a best fit with the corresponding teeth between the virtual model of the actual teeth and the electronic plan. It has been found that the comparison and evaluation after a best fit matching provides a truer and more accurate measurement of the treatment that removes possible problems introduced by matching the virtual model of an entire arch wherein individual teeth may not be accurately oriented and positioned. The algorithm is applied iteratively and it has been found that application of between 5 and 10 iterations provide more than satisfactory results.

Figure 8:
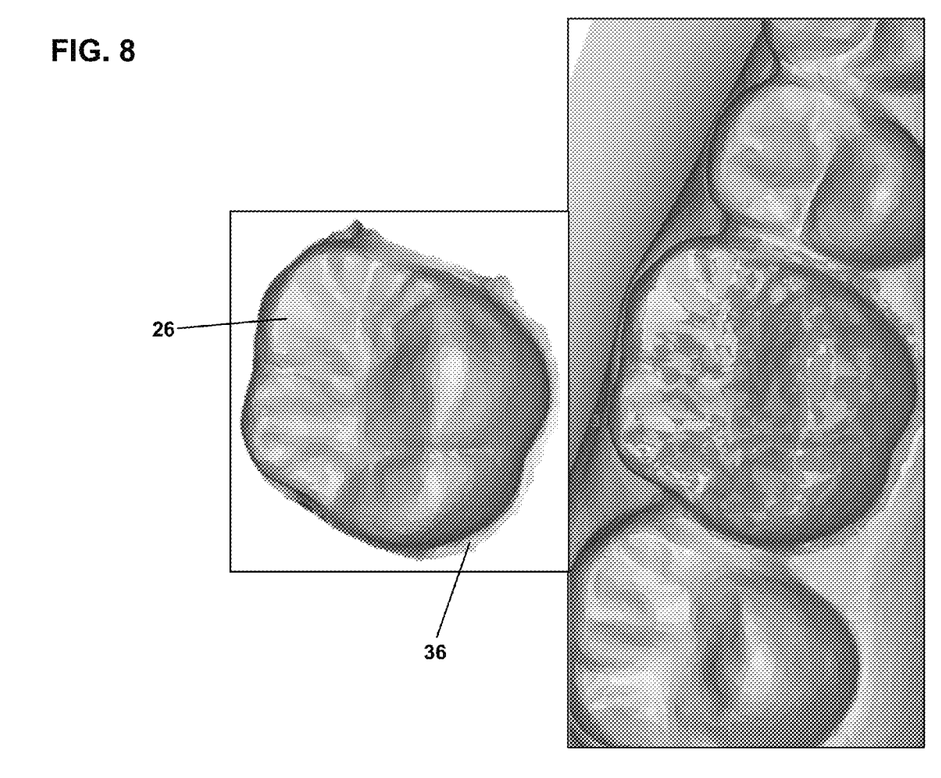
FIG. 8 is a side view of the virtual model of the tooth and coordinate system shown in FIG. 3 after a best fit matching process.
Figure 9:
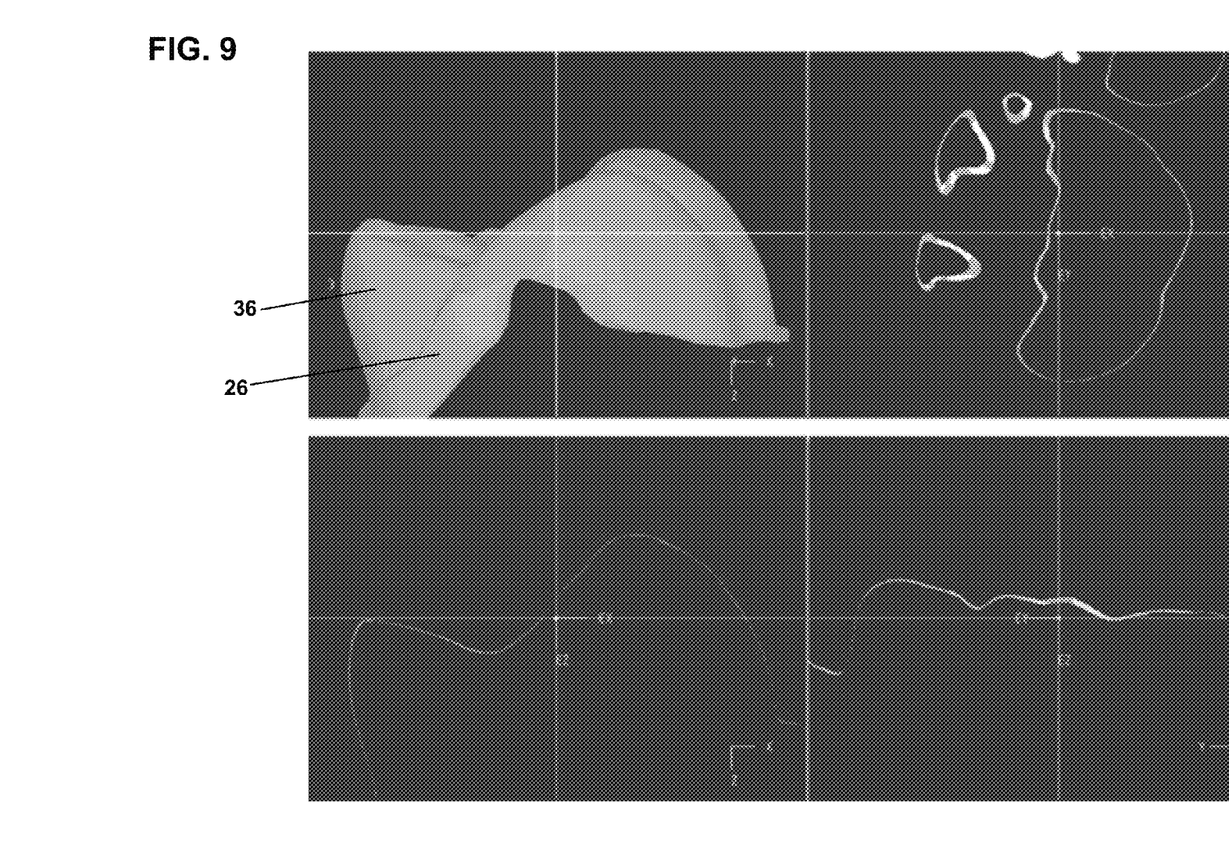
FIG. 9 is a perspective view of the electronic representation of the desired arch configuration shown in FIG. 4 being superimposed to the virtual model shown in FIG. 2 after a best fit matching process.
Figure 10:
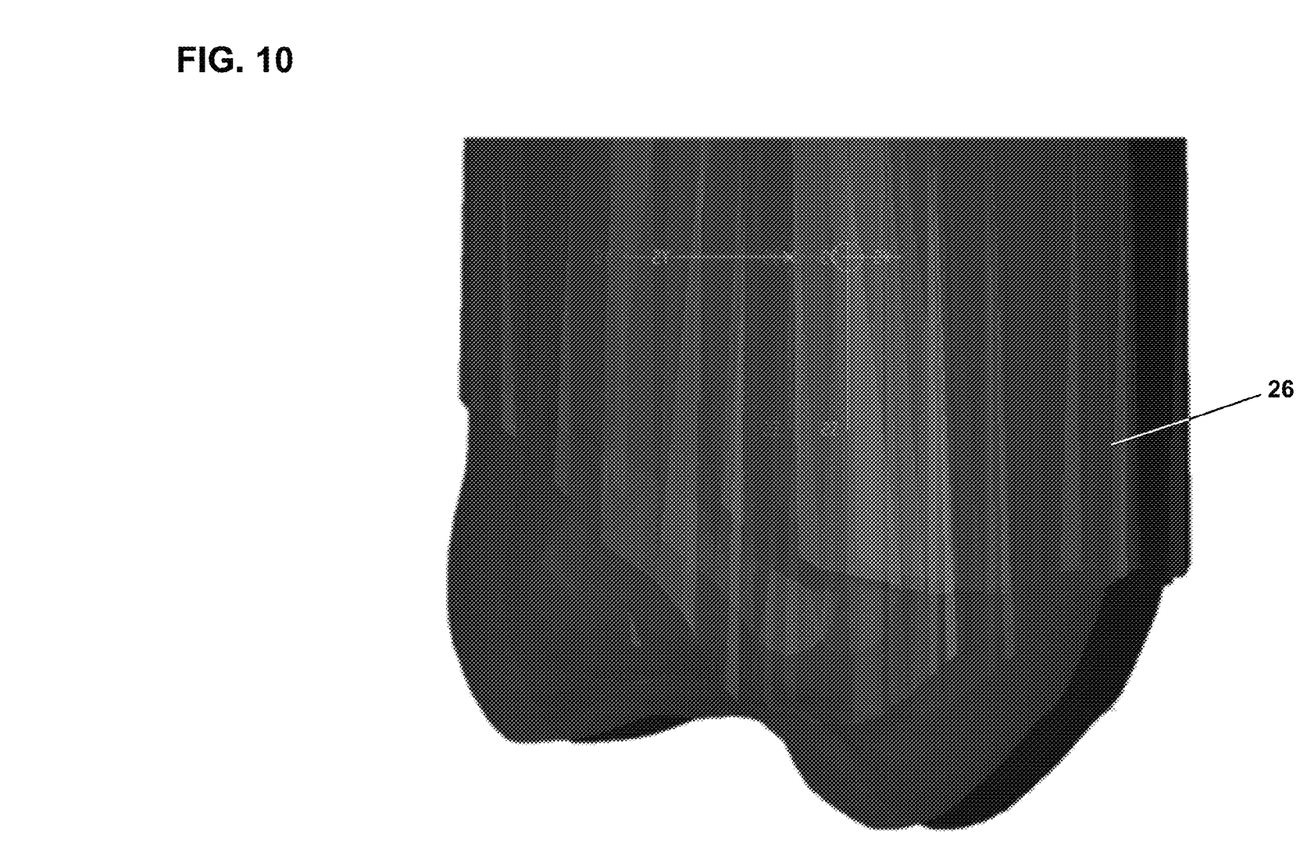
FIG. 10 is a cross-sectional view of a virtual model of a portion of a tooth with differences shown between the desired position and actual position following treatment and after a best fit matching process.

As shown in FIG. 8, after the best fit process, the three dimensional coordinate system for the tooth 26 shifts from that shown in FIG. 3. The shifted tooth 36 is then superimposed with the electronic plan tooth and virtual differences are measured, such as shown in FIG. 9. The portion of the tooth with the mesh of measurement points may then be represented as shown in FIG. 10 with the variance distances represented, for example, by different colors. These variances may then be assigned a numerical value so that a numerical score may be assigned. A table of data is created representing the measurements and the scores assigned, including extrapolated measurements reflecting the various grading criteria.

The assigned scores can be used for multiple purposes including grading for certification of practitioners. In addition, the assigned scores can be used for comparing the needs of different patients and ranking the need for treatment. Where dental care is limited or priority must be assigned to each patient, the present invention provides a more objective measure than is possible with prior art methods and systems. The objective ranking can also be used for evaluation of the likelihood of success and to evaluate cost effectiveness for various patient needs. The objective scoring also allow for making a virtual model after a period of time has passed and performing an evaluation. Such subsequent evaluation provides for studying the effects of normal usage over time and/or growth as compared to an idealized model.

It can be appreciated that cone beam computer tomography and digitizing of a plaster cast through precision digital scanning eliminates measurement differences and inaccuracies due to imprecision with location of the measuring devices. Moreover, the program may be run quickly without requiring individual graders to manually perform measurements and the raw data or processed data with scores may be supplied to all graders.

It can further be appreciated that inaccuracies due to difficulties in superimposing a patient's arch onto a proposed arch following orthodontic treatment are compensated with a best match process being applied to each of the teeth. Inaccuracies from consistently locating landmarks are also eliminated with the present invention. This system also eliminates the need for maintaining plaster casts for evaluation and grading and difficulties with storing and transporting such plaster casts for the measurement and grading.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A method of quantifying corrective tooth positioning, comprising:
   creating a first virtual model of an actual position of a patient's teeth;
   creating a second virtual model of a preferred position of a patient's teeth after orthodontic treatment; superimposing the first and second virtual models;
   performing a best fit process for fitting corresponding teeth of the first and second virtual models and moving one of the teeth accordingly;
   evaluating the differences in position of the teeth of the first and second virtual models;
   scoring the differences and assigning a score to each patient; and
   prioritizing patient needs based on the score assigned.

2. A method according to claim 1, wherein the first virtual model is created by scanning the patient's teeth with a three dimensional cone beam scanner.

3. A method according to claim 1, further comprising a score based on the differences between the second virtual model and another of the virtual models.

4. A method according to claim 3, wherein the score is based on parameters related to changes in three dimensions and rotations about three axes in a coordinate system.

5. A method according to claim 1, wherein contact points between upper and lower teeth in the virtual models are compared and evaluated.

6. A method according to claim 1, further comprising assigning a score to the differences in position of the teeth of the first and second virtual models.

7. A method of evaluating corrective tooth positioning, comprising:
   creating a first virtual model of a preferred position of the teeth after orthodontic treatment;
   creating a second virtual model of an actual position of the teeth after treatment;
   superimposing the first and second virtual models; performing a best fit process for fitting corresponding teeth of the first and second virtual models and moving one of the teeth accordingly;
   evaluating the differences in position of the teeth of the first and second virtual models; and
   applying a three dimensional coordinate system to individual teeth and shifting the three dimensional coordinate system by the closest point algorithm.

8. A method according to claim 7, wherein the best fit process comprises performing a closest point algorithm.

9. A method according to claim 8, wherein the closest point analysis comprises an iterative process.

10. A method according to claim 7, further comprising creating a pretreatment virtual model of a portion of the patient's teeth prior to treatment and wherein the first virtual model is based on the pretreatment virtual model.

11. A method according to claim 7, wherein the first and second virtual models are created by gaining a digital scan of the patient's teeth.

12. A method according to claim 7, wherein different ranges of differences in position are represented by different colors.

13. A method according to claim 7, wherein a mesh of measurement locations are assigned to each tooth.

14. A method according to claim 7, wherein the second virtual model is created by scanning the patient's teeth with a three dimensional cone beam scanner.

15. A method of evaluating corrective tooth positioning, comprising:
   creating a first virtual model of a portion of the patient's teeth prior to treatment;
   creating a second virtual model of a preferred position of the teeth after orthodontic treatment;
   creating a third virtual model of an actual position of the teeth after treatment;
   superimposing the second and third virtual models;
   performing a closest point algorithm and fitting corresponding teeth of the second and third superimposed virtual models and moving at least one of the teeth accordingly;
   evaluating the differences in position of the teeth of the first and second virtual models; and
   creating a fourth virtual model at a time subsequent to creating the third virtual model and comparing the fourth virtual model to the second virtual model.

16. A method according to claim 15, further comprising comparing the second and third virtual models.

* * * * *